United States Patent
Otake et al.

(10) Patent No.: US 12,372,484 B2
(45) Date of Patent: Jul. 29, 2025

(54) CABLE INSPECTION DEVICE AND CABLE INSPECTION METHOD

(71) Applicant: RIKEN, Wako (JP)

(72) Inventors: Yoshie Otake, Wako (JP); Yoshimasa Ikeda, Wako (JP); Yuichi Yoshimura, Wako (JP); Takao Hashiguchi, Wako (JP); Maki Mizuta, Wako (JP); Hirokazu Kitagawa, Nagoya (JP); Kenta Kato, Nagoya (JP)

(73) Assignee: RIKEN, Wako (JP)

( * ) Notice: Subject to any disclaimer, the term of this patent is extended or adjusted under 35 U.S.C. 154(b) by 220 days.

(21) Appl. No.: 18/008,747

(22) PCT Filed: Jun. 18, 2021

(86) PCT No.: PCT/JP2021/023242
§ 371 (c)(1),
(2) Date: Dec. 7, 2022

(87) PCT Pub. No.: WO2021/261405
PCT Pub. Date: Dec. 30, 2021

(65) Prior Publication Data
US 2023/0213462 A1    Jul. 6, 2023

(30) Foreign Application Priority Data
Jun. 22, 2020   (JP) .................. 2020-106799

(51) Int. Cl.
*G01N 23/20008* (2018.01)
*G01N 33/2045* (2019.01)

(52) U.S. Cl.
CPC ... *G01N 23/20008* (2013.01); *G01N 33/2045* (2019.01)

(58) Field of Classification Search
CPC ...... G01N 23/18; G01N 23/204; G01N 23/09; G01N 23/20
See application file for complete search history.

(56) References Cited

U.S. PATENT DOCUMENTS 10,241,061 B2 *  3/2019  Otake ................ G01V 5/222
2019/0265176 A1 *  8/2019  Jordan ............... G01N 23/05
(Continued)

FOREIGN PATENT DOCUMENTS

JP    07-306166 A    11/1995
JP    2008-082779 A   4/2008
(Continued)

OTHER PUBLICATIONS https://wwwndc.jaea.go.jp/jendl/j40/J40_J.html#/index2; and URL 2 for data on the scattering cross section of neutrons to iron: https://wwwndc.jaea.go.jp/j40fig/jpeg/fe056_f1.jpg.
(Continued)

*Primary Examiner* — Oluseye Iwarere
*Assistant Examiner* — Miya Downing
(74) *Attorney, Agent, or Firm* — Volpe Koenig

(57) ABSTRACT

A cable inspection device non-destructively inspects a cable used for supporting a bridge. The cable inspection device includes a neutron source and a neutron detection device. The neutron source emits neutrons to the cable. The neutron detection device includes a detection surface arranged outside the cable, and detects target neutrons and measures the number of the detected target neutrons when neutrons are emitted to the cable. The target neutrons are among the neutrons released from the cable and incident on the detection surface, and each have an energy equal to or lower than a predetermined value that is lower than an energy of a fast neutron.

11 Claims, 17 Drawing Sheets

(56) References Cited

U.S. PATENT DOCUMENTS

| | | |
|---|---|---|
| 2019/0277825 A1 | 9/2019 | Staal et al. |
| 2021/0270993 A1* | 9/2021 | Cederwall ............ G08B 21/182 |

FOREIGN PATENT DOCUMENTS

| | | |
|---|---|---|
| JP | 2010-151646 A | 7/2010 |
| JP | 2013-245496 A | 12/2013 |
| JP | 2017-049171 A | 3/2017 |
| JP | 2018-119970 A | 8/2018 |
| WO | 2017/039017 A1 | 3/2017 |

OTHER PUBLICATIONS

International Preliminary Report on Patentability issued on Dec. 13, 2022 for PCT International Application No. PCT/JP2021/023242.

Office Action issued on Jun. 21, 2024 for Japanese Patent Application No. 2020-106799.

Extended European Search Report issued on Nov. 17, 2023 for European Patent Application No. 21829123.5.

Noyan, I.C., et al., "Measurement of Strain/Load Transfer in Parallel Seven-wire Strands with Neutron Diffraction," Experimental Mechanics, (2010).

Brugger, A., et al., "Designing and Validating Parallel Wire Suspension Bridge Wire Strands for Neutron Diffraction Stress Mapping," Materials Science Forum, (2017).

* cited by examiner

A: 2500 OR LARGER AND SMALLER THAN 3000
B: 2000 OR LARGER AND SMALLER THAN 2500
C: 1500 OR LARGER AND SMALLER THAN 2000
D: 1000 OR LARGER AND SMALLER THAN 1500
E: SMALLER THAN 1000

C: 1500 OR LARGER AND SMALLER THAN 2000
D: 1000 OR LARGER AND SMALLER THAN 1500
E: SMALLER THAN 1000

A: 7 OR LARGER AND SMALLER THAN 8
B: 6 OR LARGER AND SMALLER THAN 7
C: 4 OR LARGER AND SMALLER THAN 6
D: 2 OR LARGER AND SMALLER THAN 4

E: 2 OR LARGER AND SMALLER THAN 3
F: SMALLER THAN 2

E: 2 OR LARGER AND SMALLER THAN 3
F: SMALLER THAN 2

C: 4 OR LARGER AND SMALLER THAN 6
G: 3 OR LARGER AND SMALLER THAN 4
H: SMALLER THAN 3

A: 1.6 OR LARGER AND SMALLER THAN 2.0
B: 1.4 OR LARGER AND SMALLER THAN 1.6
C: 1.0 OR LARGER AND SMALLER THAN 1.4

B: 1.4 OR LARGER AND SMALLER THAN 1.6
D: 1.2 OR LARGER AND SMALLER THAN 1.4
E: 1.0 OR LARGER AND SMALLER THAN 1.2

F: 1.2 OR LARGER AND SMALLER THAN 1.3
G: 1.1 OR LARGER AND SMALLER THAN 1.2
H: 1.0 OR LARGER AND SMALLER THAN 1.1

B: 1.4 OR LARGER AND SMALLER THAN 1.6
D: 1.2 OR LARGER AND SMALLER THAN 1.4
E: 1.0 OR LARGER AND SMALLER THAN 1.2

CABLE INSPECTION DEVICE AND CABLE INSPECTION METHOD

TECHNICAL FIELD

The present invention relates to a device and a method for inspecting a cable used for supporting a bridge such as a cable-stayed bridge, a suspension bridge, or an extradosed bridge.

BACKGROUND ART

Cables are used for supporting various types of bridges. For example, in a cable-stayed bridge, cables are stretched between a tower and a bridge girder, and the bridge girder is supported by the tower via a plurality of the cables. Each of cables supporting various types of bridges such as a cable-stayed bridge, a suspension bridge, and an extradosed bridge is configured so as to include a bundle of many metal wires and a cover layer (e.g., a protective tube) that covers the bundle.

For such bridges, inspection is regularly performed on whether damage or fracture exists in metal wires inside cables. According to Patent Literature 1 for example, a coil and a circuit are prepared, the coil generates eddy current in a cable, and the circuit measures an impedance of the coil. Based on the measured impedance value, it is determined whether damage or fracture exists in metal wires (steel wires) inside the cable.

CITATION LIST

Patent Literatures

Patent Literature 1: Japanese Patent Application Laid-open Publication No. 2018-119970

NON-PATENT LITERATURES

Non-Patent Literature 1: URL 1 for data on the scattering cross section of neutrons to iron: https://wwwndc.jaea.go.jp/jendl/j40/J40_J.html#index2; and URL 2 for data on the scattering cross section of neutrons to iron: https://wwwndc.jaea.go.jp/j40fig/jpeg/fe056_f1.jpg

SUMMARY OF INVENTION

Technical Problem

Damage or fracture of metal wires that constitute a cable is caused by rusting of the metal wires. Accordingly, it is desirable to inspect whether water causing rusting of metal wires exists inside a cable. When water is detected as a result of the inspection on existence or nonexistence of water causing rusting of metal wires, an appropriate measure can be taken such that water does not exist inside the cable. This can reduce a possibility that the metal wires are damaged or fractured.

The present invention has been made based on such a viewpoint. In other words, an object of the present invention is to provide a cable inspection device and a cable inspection method that can non-destructively inspect whether water exists inside a cable used for supporting a bridge, from outside the cable.

Solution to Problem

In order to accomplish the above-described object, a cable inspection device according to the present invention is a device for non-destructively inspecting a cable used for supporting a bridge,
  the cable being configured so as to include a plurality of metal wires,
  the cable inspection device including:
  a neutron source that emits neutrons to the cable; and
  a neutron detection device that includes a detection surface arranged outside the cable, and detects target neutrons and measures the number of the detected target neutrons when the neutron source emits neutrons to the cable, wherein the target neutrons are among the neutrons released from the cable and incident on the detection surface, and each have an energy equal to or lower than a predetermined value that is lower than an energy of a fast neutron.

A cable inspection method according to the present invention is a method for non-destructively inspecting a cable used for supporting a bridge, the method including:
  (A) arranging a neutron source and a neutron detector in relation to the cable that is configured so as to include a plurality of metal wires;
  (B) by the neutron source, emitting neutrons to an irradiation region on an outer peripheral surface of the cable; and
  (C) detecting target neutrons and measures the number of the detected target neutrons, wherein the target neutrons are among the neutrons released from the cable as a result of the emitting and incident on a detection surface of the neutron detector, and each have an energy equal to or lower than a predetermined value that is lower than an energy of a fast neutron.

Advantageous Effects of Invention

According to the present invention, in the case where water exists inside the cable, when neutrons are emitted to the cable, the neutrons react with the water, and thus, reduce their own energies. For this reason, based on the number of the detected target neutrons corresponding to the neutrons having the reduced energies, it can be determined whether water exists inside the cable.

DESCRIPTION OF EMBODIMENTS

The following describes embodiments of the present invention, with reference to the drawings. The same reference sign is allocated to the corresponding part in each of the drawings, and duplicate description is omitted.

(Cable-Stayed Bridge as One Example of Inspection Target)

Figure 1:
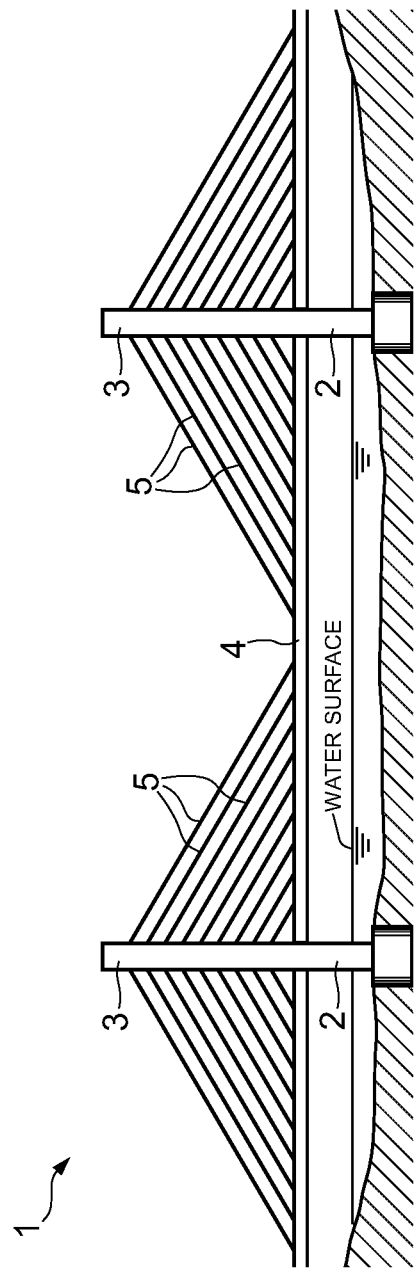
FIG. 1 illustrates one example of a cable-stayed bridge as an inspection target of a cable inspection device according to the present invention.

FIG. 1 illustrates one example of a cable-stayed bridge 1 as an inspection target of a cable inspection device 10 according to the present invention. The cable-stayed bridge 1 includes a pier 2 and a bridge girder 4 supported by the pier 2. The cable-stayed bridge 1 is supported by a plurality of cables 5. Specifically, each cable 5 is stretched between a tower 3 provided on the pier 2 and the bridge girder 4, and supports the bridge girder 4. In other words, the bridge girder 4 is supported by the tower 3 via the cables 5. In FIG. 1, respective both end portions of each cable 5 are coupled to the tower 3 and the bridge girder 4. The one end portion of each cable 5 may be coupled to the bridge girder 4 via a reinforcement member (e.g., a truss) of the bridge girder 4.

Figure 2:
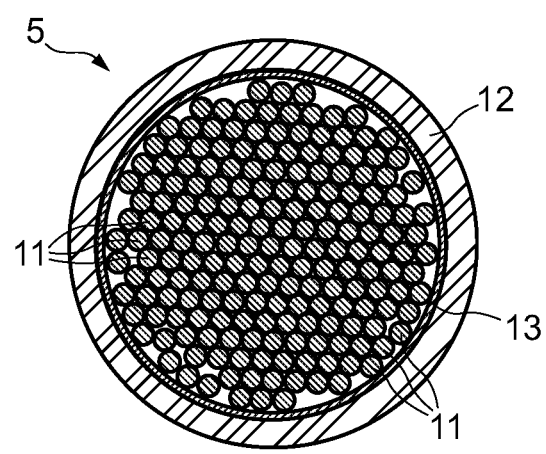
FIG. 2 is a cross-sectional view of one cable.

FIG. 2 is a cross-sectional view of one cable 5. The cable 5 is configured so as to include a plurality (e.g., a large number) of metal wires 11 and a cover layer 12. Each of the metal wires 11 is, for example, a steel wire formed of steel whose main component is iron. The cover layer 12 covers an entire outer periphery of a bundle of a plurality of the metal wires 11. The cover layer 12 extends in a longitudinal direction of the cable 5. The cover layer 12 is formed of a highly weather-resistant material (e.g., synthetic resin such as polyethylene or fluororesin). The cover layer 12 may be a protective tube that accommodates the bundle of the metal wires 11 inside. The cable 5 may include a restriction portion 13 that bundles the metal wires 11 inside the cover layer 12, as illustrated in FIG. 2. A diameter of the bundle of the metal wires 11 may be equal to or larger than 100 mm, for example, but is not limited to this. Each of cables that support other bridges such as a suspension bridge and an extradosed bridge also has the same configuration as that of the above-described cable 5. Accordingly, the cable 5 described below has the above-described configuration, and may be a cable that supports the cable-stayed bridge 1, or may be a cable that supports a different bridge such as a suspension bridge or an extradosed bridge.

First Embodiment (Configuration of Cable Inspection Device)

Figure 3:
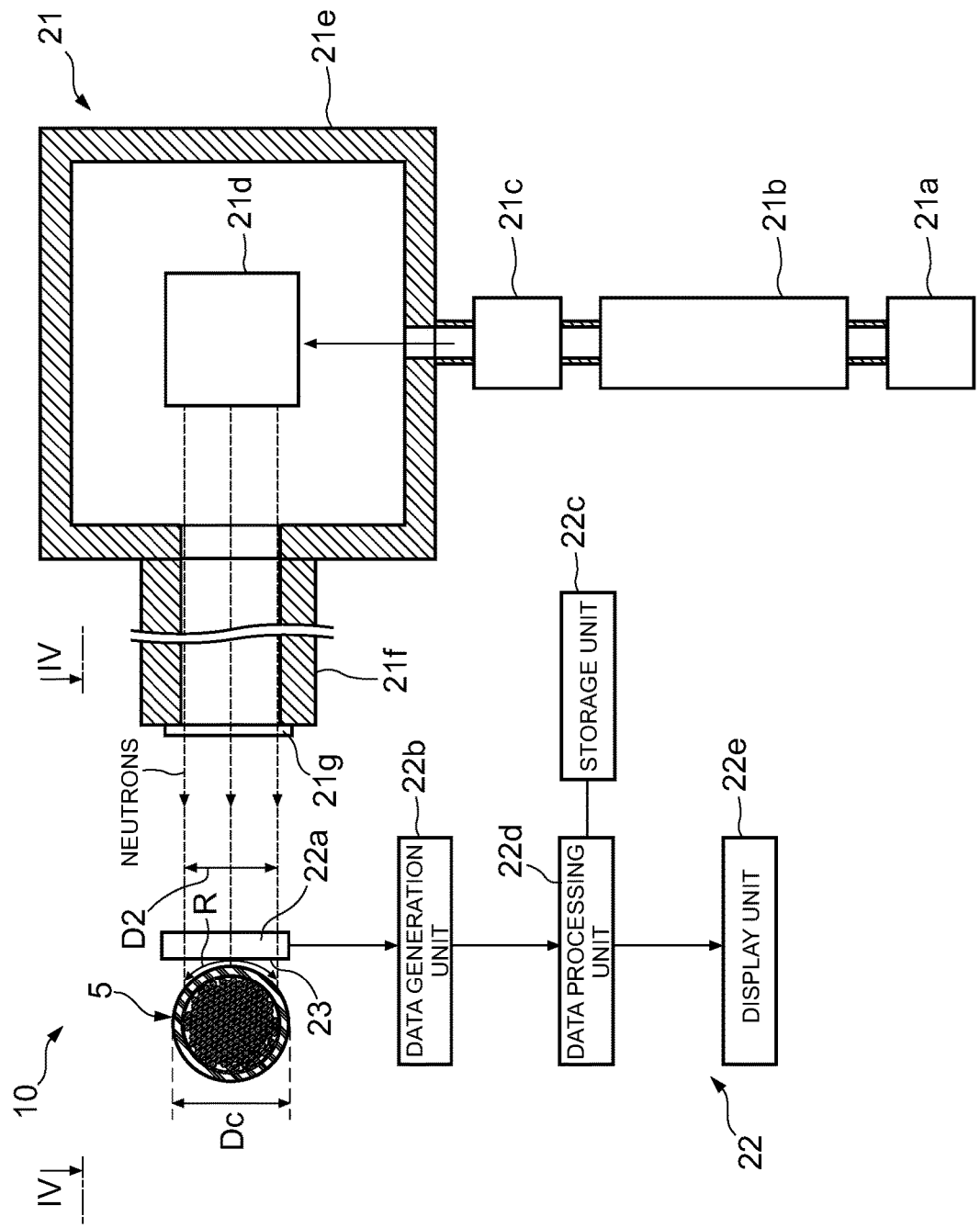
FIG. 3 illustrates a configuration example of a cable inspection device according to a first embodiment of the present invention.
Figure 4:
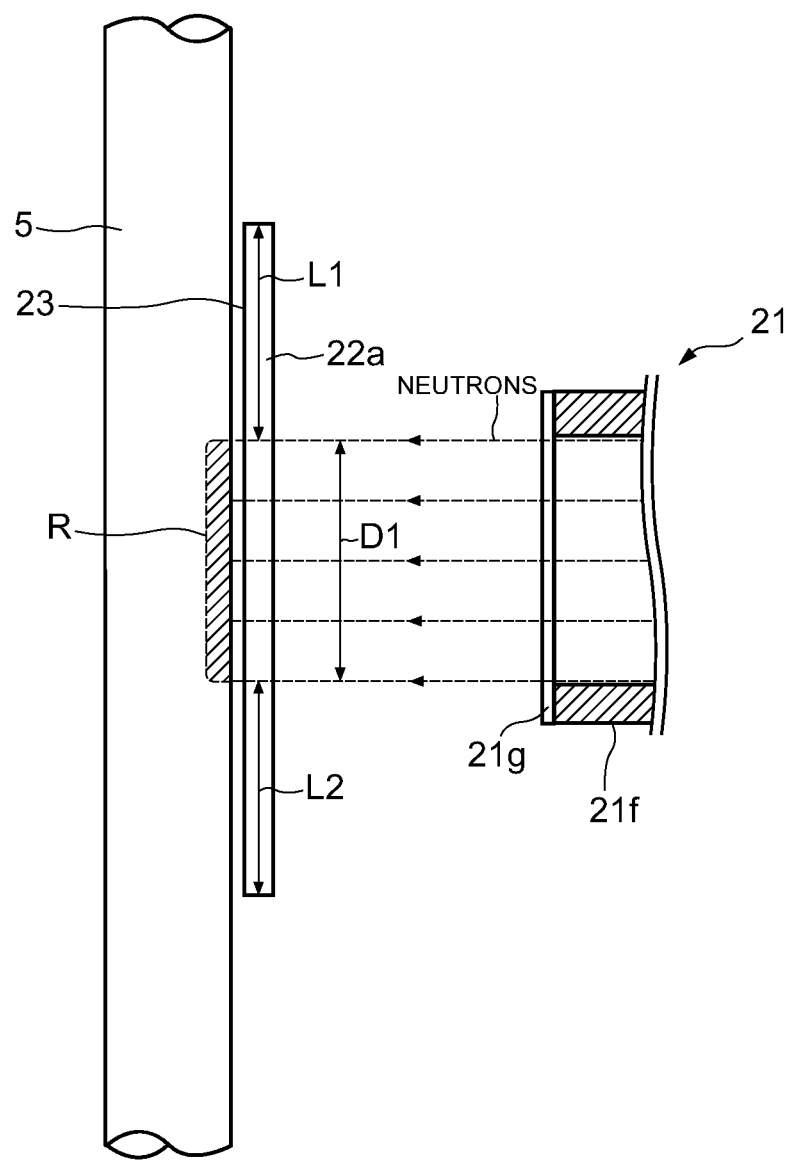
FIG. 4 is an illustration viewed in a direction of the arrows IV-IV in FIG. 3.

FIG. 3 illustrates a configuration example of a cable inspection device 10 according to a first embodiment of the present invention. FIG. 4 is an illustration viewed in a direction of the arrows IV-IV in FIG. 3. The cable inspection device 10 is a device for non-destructively inspecting the cable 5 that supports an existing bridge. More specifically, the cable inspection device 10 is used for inspecting whether water exists inside the cable 5. The cable inspection device 10 emits neutrons to the cable 5, and detects neutrons that are among neutrons released from the cable 5 included in the emitted neutrons and that each have energy equal to or lower than a predetermined value. The predetermined value is lower than energy of a fast neutron. The cable inspection device 10 includes a neutron source 21 and a neutron detection device 22.

The neutron source 21 emits, from outside the cable 5, neutrons to the cable 5 as an inspection target. The neutron source 21 may be configured so as to emit a pulsed neutron beam having a minute pulse time width (e.g., approximately 0.1 millisecond), or may be configured so as to continuously emit neutrons. The neutron source 21 emits neutrons to the cable 5 in a direction intersecting with (e.g., perpendicular to) the longitudinal direction (hereinafter, simply referred to also as the cable longitudinal direction) of the cable 5.

In an example of FIG. 3, the neutron source 21 includes an ion source 21a, an acceleration device 21b, a beam adjuster 21c, a target 21d, a container 21e, and a tubular shielding member 21f. The ion source 21a generates hydrogen ions (protons), for example. The acceleration device 21b accelerates the protons generated by the ion source 21a. The beam adjuster 21c includes a plurality of magnetic field coils that adjust, to the target 21d, a direction and a spread of the proton beam accelerated by the acceleration device 21b. After passing the beam adjuster 21c, the proton beam is incident on the target 21d. As a result, neutrons are generated by reaction between the protons and the target 21d (e.g., beryllium). The target 21d is arranged in the container 21e formed of a material difficult for neutrons and gamma rays to pass through. In the container 21e, a hole is formed so as to penetrate from an outer surface of the container 21e to its inside. The tubular shielding member 21f for neutron emission is attached to this hole. The tubular shielding member 21f is formed of a material difficult for neutrons to pass through. The neutrons generated from the target 21d pass through an inside of the tubular shielding member 21f, and are thus released as a neutron beam so as to be emitted to the cable 5.

The neutron source 21 can be configured small in size to such an extent that the neutron source 21 can be transported. Thus, the neutron source 21 can be transported to a bridge as an inspection target, and can be arranged at a position for emitting neutrons to the cable 5.

The neutron detection device 22 includes a detection surface 23 arranged outside the cable 5. When the neutron source 21 emits neutrons to the cable 5, the neutron detection device 22 detects neutrons (hereinafter, simply referred to also as target neutrons) that are among neutrons released from the cable 5 and then incident on the detection surface 23 and that each have energy equal to or lower than the predetermined value. This predetermined value is lower than energy ($10^5$ eV) of a fast neutron. The neutron detection device 22 measures the number of the detected target neutrons.

The neutron detection device 22 includes a neutron detector 22a, a data generation unit 22b, a storage unit 22c, and a data processing unit 22d.

The neutron detector 22a includes the two-dimensional detection surface 23 for detecting neutrons from the cable 5. In the case where water exists in the cable 5, when neutrons emitted to the cable 5 enter the water inside the cable 5, the neutrons are moderated by the water, and thus reduce their own energies (e.g., become thermal neutrons). In view of this, in order to detect water inside the cable 5 as a defect, the neutron detector 22a is configured so as to detect target neutrons that are among neutrons incident on the detection surface 23 and that each have energy equal to or lower than the predetermined value. In one embodied example, this predetermined value is a value equal to or higher than 1 meV and equal to or lower than 10 eV (e.g., this predetermined value is a value within a range from several milli-electron-volts to several electron-volts eV). However, according to the present invention, the predetermined value may be a value equal to or higher than 1 eV and equal to or lower than $1\times10$ eV, or a value equal to or higher than 10 eV and equal to or lower than $1\times10^2$ eV, or a value equal to or higher than $1\times10^2$ eV and equal to or lower than $1\times10^3$ eV, or a value equal to or higher than $1\times10^3$ eV and equal to or lower than $1\times10^4$ eV, or a value within another range. An energy range of detectable neutrons varies depending on neutron detectors. Accordingly, a detector that detects neutrons each having energy within the above-described energy range may be selected as the neutron detector 22a. Alternatively, a measurement system of the neutron detector 22a may be designed so as to detect neutrons each having energy within the above-described energy range.

In the first embodiment, the detection surface 23 may be planar. At the time of inspection, the detection surface 23 is arranged so as to face an outer peripheral surface of the cable 5. Each time the target neutron is incident on the detection surface 23, the neutron detector 22a detects the target neutron, and outputs a detection signal indicating an incident position that is on the detection surface 23 and on which the target neutron is incident.

The data generation unit 22b generates and outputs detection data, based on the respective detection signals output from the neutron detector 22a. The detection data represent, for each position on the detection surface 23, the number (hereinafter, simply referred to also as the number of incident neutrons) of the target neutrons incident on this position. The data generation unit 22b may generate the detection data, based on the respective detection signals generated over a measurement period from a detection start time point to a detection end time point. In the case where the neutron source 21 emits pulsed neutrons to the cable 5, the detection start time point may be a time point when the neutron source 21 starts to emit the pulsed neutrons. The detection end time point may be an expected time point when the total number of the target neutrons incident on the detection surface 23 of the neutron detector 22a in a short unit time becomes sufficiently smaller than that at the peak time, and may be predetermined by estimation. The detection data indicate, for each position on the detection surface 23, the total number of the target neutrons incident on this position in the measurement period. A length of the measurement period is, for example, approximately 10 minutes, but is not limited to this.

The storage unit 22c stores reference data that correspond to the detection data and that are acquired for a sound cable having the same structure as that of the inspection-target cable 5. For example, the above-described detection data are acquired by the cable inspection device 10 for a cable that has the same structure (materials, dimensions, and the like) as that of the inspection-target cable 5 and that does not contain a defective portion such as water inside, and the thus-acquired detection data are used as the reference data. In this case, the reference data and the detection data detected at the time of actual inspection are preferably acquired by the same cable inspection device 10, for cables having the same structure under the same conditions In the present embodiment, the data processing unit 22d generates and outputs difference data (processed data) that represent, for each position on the detection surface 23, a difference between the number of incident neutrons in the reference data and the number of the incident neutrons in the detection data.

A display unit 22e displays, on its screen, the difference data output from the data processing unit 22d. For example, the display unit 22e displays, as the difference data, the two-dimensional detection surface 23 and an indication (e.g., a color, shade, or a numerical value) that represents, at each position on the detection surface 23, the above-described difference of this position. The difference data are output to the display unit 22e in this example, but may be output to another part (e.g., an appropriate storage device).

<Energy of Emitted Neutron>

Hereinafter, the energy of the neutron that is resonantly scattered due to the metal wire 11 when the neutron is made incident on the metal wire 11 is referred to as the resonance scattering energy.

In the present embodiment, the neutron source 21 emits, to the cable 5, neutrons including neutrons that each have the resonance scattering energy. In this case, neutrons that constitute a predetermined proportion of the neutrons emitted to the cable 5 by the neutron source 21 each have the resonance scattering energy. Here, the predetermined proportion may be at least 15%, at least 30%, at least 50%, at least 70%, or at least 80%, but may be other values.

The metal wire 11 may be a steel wire made of steel. A main constituent of the steel is iron ($^{56}$Fe). In this regard, the resonance scattering energy with respect to iron ($^{56}$Fe) is equal to or higher than approximately 10 keV and equal to or lower than approximately 8 MeV (this range is based on data from Non-Patent Literature 1, for example). Accordingly, when the metal wire 11 is a steel wire, the resonance scattering energy is an energy within this range.

Figure 5:
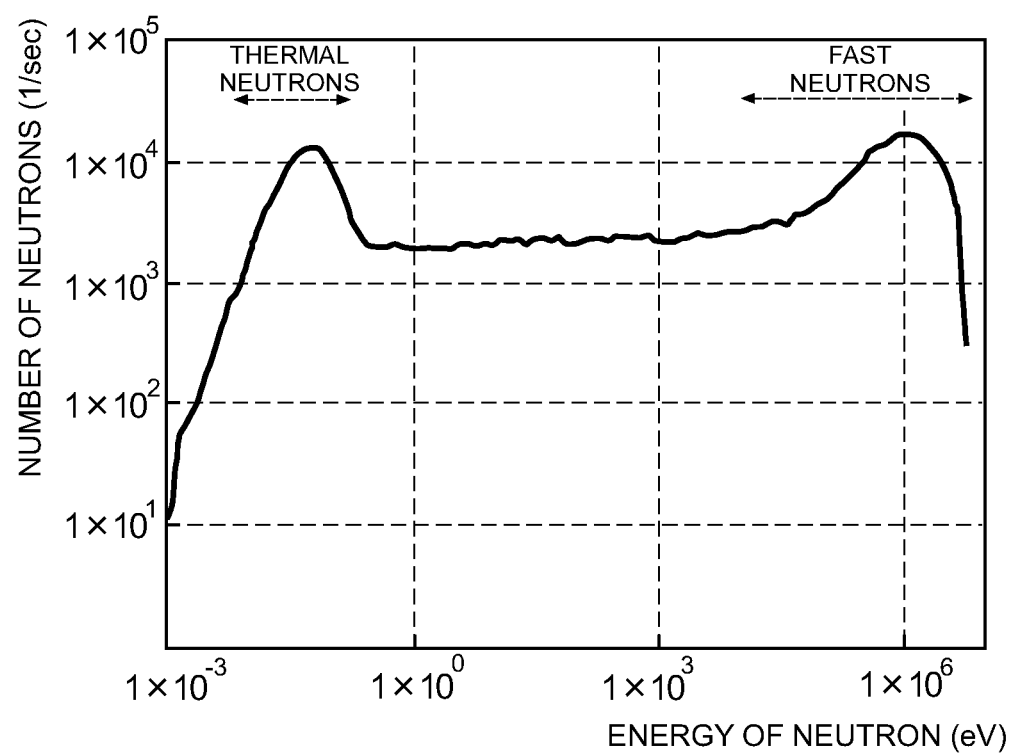
FIG. 5 illustrates one example of an energy spectrum of neutrons that are emitted from a neutron source and that are not moderated by a moderator (moderating member).

FIG. 5 illustrates one example of an energy spectrum of neutrons that are emitted from the above-described neutron source 21 and that are not moderated by a moderator (moderating member). In FIG. 5, the horizontal axis indicates an energy (kinetic energy) of the neutron, and the vertical axis indicates the number of neutrons passing through a unit sectional area (cm$^2$) per unit time (second).

In connection with FIG. 5, neutrons are classified into fast neutrons, thermal neutrons, and the like, depending on their energies. Generally, energy ranges of the fast neutron and the thermal neutron are not strictly defined. In the present application, the fast neutron may be a neutron having an energy equal to or higher than $1\times10^5$ (100 keV) in practice (e.g., in an embodied example), but is not limited to this. In the present application, the thermal neutron may be a neutron having an energy equal to or lower than several tens of milli-electron-volts (e.g., 0.05 eV), but is not limited to this. In this case, a neutron having an energy equal to or lower than 0.01 eV may belong to the thermal neutrons, or may belong to cold neutrons instead of belonging to the thermal neutrons. The resonance scattering energy with respect to $^{56}$Fe belongs to the fast neutrons.

The neutron source 21 is configured so as to emit, to the cable 5, neutrons including a large number of the fast neutrons. For example, the neutron source 21 may be configured so as to emit, to the cable 5, neutrons substantially including only the fast neutrons out of the thermal neutrons and the fast neutrons. In this case, the emitted neutrons may include epithermal neutrons. The fast neutrons constituting the emitted neutrons preferably include a large number of neutrons each having the resonance scattering energy (e.g., the above-described resonance scattering energy with respect to $^{56}$Fe). In order to emit, to the cable 5, neutrons substantially including only the fast neutrons out of the thermal neutrons and the fast neutrons, the neutron source 21 may include a thermal neutron shielding member 21g arranged on a path through which neutrons travel from the target 21d to the cable 5. The neutron source 21 may emit the neutrons to the cable 5 via the thermal neutron shielding member 21g. In this case, the neutrons immediately before passing through the thermal neutron shielding member 21g may have the energy spectrum illustrated in FIG. 5, for example.

<Positional Relation Among Cable, Neutron Source, and Neutron Detector>

The sectional area (hereinafter, simply referred to also as the neutron beam sectional area) of the neutron beam immediately before being made incident on the cable 5 may have a dimension D1 in the cable longitudinal direction (the vertical direction in FIG. 4) and a dimension D2 in a direction (the vertical direction in FIG. 3) perpendicular to the cable longitudinal direction, such that the dimension D1 is larger than the dimension D2. In this case, a shape of the neutron beam sectional area may be, for example, substantially rectangular or substantially elliptical (substantially rectangular in FIG. 4). The dimension D2 may be equal to or smaller than an outer diameter Dc of the cable 5 (e.g., may be equal to the outer diameter of the cable 5 or equal to an outer diameter of a bundle of the metal wires 11). The neutron beam sectional area is preferably within an area of the cable 5 when viewed in a traveling direction of the neutron beam. In FIG. 4, the hatched part is an irradiation region R that is on the outer peripheral surface of the cable 5 and that is irradiated with the neutron beam.

When the neutrons each having the resonance scattering energy are emitted to the cable 5, these neutron travel inside the metal wires 11 while being resonantly scattered in the metal wires 11, so that a large number of the scattered neutrons are released out of the cable 5 also from positions distant in the cable longitudinal direction from the irradiation region R on which the neutron beam to the cable 5 is made incident. Accordingly, at the time of inspection, the neutron detector 22a may be arranged such that in the cable longitudinal direction, a part of the detection surface 23 is positioned within the irradiation region R, and a remaining part of the detection surface 23 is positioned outside the irradiation region R. Alternatively, at the time of inspection, the neutron detector 22a may be arranged such that in the cable longitudinal direction, the entire detection surface 23 is positioned outside the irradiation region R.

In such a case, L denotes a length of the part (hereinafter, referred to a non-incident part) that is included in the detection surface 23 and that extends, outside the irradiation region R, continuously in the cable longitudinal direction from a boundary between an outside of the irradiation region R and an inside of the irradiation region R. The length L may be equal to or larger than the outer diameter Dc of the cable 5 or be equal to or larger than the outer diameter of the bundle of the metal wires 11 (e.g., L may be equal to or larger than two times, three times, five times, or seven times either of these outer diameters). In FIG. 4, the detection surface 23 includes the non-incident parts positioned on both sides in the cable longitudinal direction and having respective lengths L1 and L2 as the lengths L.

<Arrangement of Neutron Detector in Peripheral Direction of Cable>

The following describes an arrangement of the neutron detector 22a in a peripheral direction of the cable 5. When the neutron detector 22a is arranged near a water region that is inside the cable 5 and where water exists, the neutron detector 22a detects a large number of the target neutrons from this water region. As a result, it is possible to more reliably detect that water exists inside the cable 5.

Figure 6A:
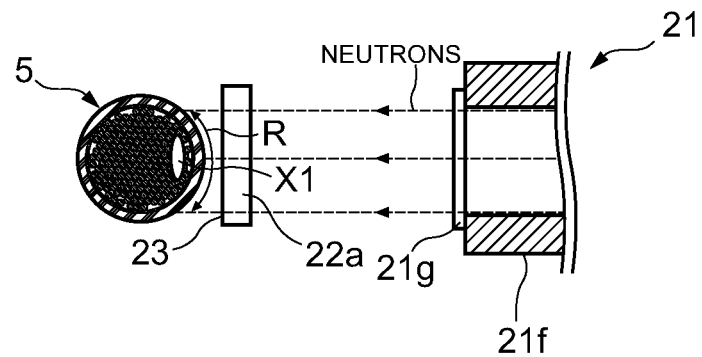
FIG. 6A to FIG. 6D illustrate arrangement examples of a neutron detector.

FIG. 6A corresponds to a part of FIG. 3, and FIG. 6B to FIG. 6D illustrates the cases where a position of the neutron detector 22a is changed from the case of FIG. 6A while positions of the neutron source 21 and the cable 5 are not changed. In FIG. 6A to FIG. 6D, X1 to X4 denote assumed water regions where water exists.

Arrangement positions for the neutron detector 22a include the following front position, opposite position, and intermediate position. Hereinafter, the peripheral direction of the cable 5 is referred to simply as the peripheral direction, and a radial direction of the cable 5 is referred to simply as the radial direction.

The front position is a position that faces the irradiation region R (e.g., a center of the irradiation region R in the peripheral direction) in the radial direction.

The opposite position is a position that faces, in the radial direction, a part (hereinafter, referred to as an opposite side part) that is on the outer peripheral surface of the cable 5 and that is positioned on an opposite side of the irradiation region R (e.g., the center of the irradiation region R in the peripheral direction).

The intermediate position is an intermediate position between the front position and the opposite position in the peripheral direction.

Figure 6B:
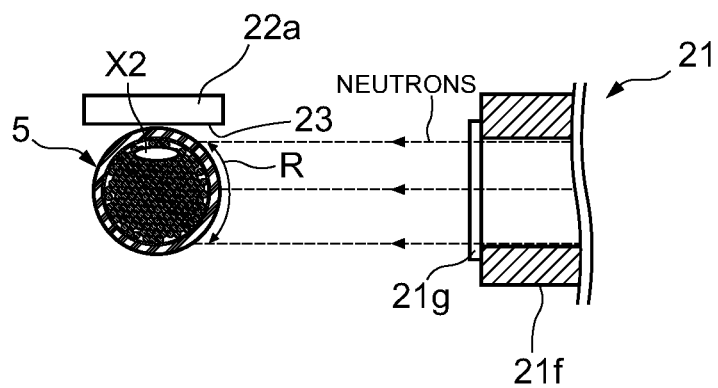
Figure 6C:
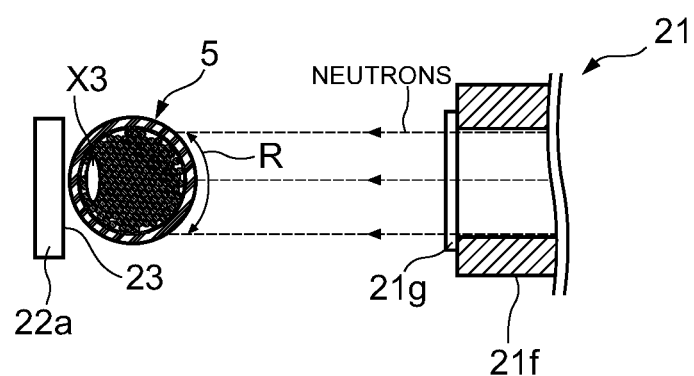
Figure 6D:
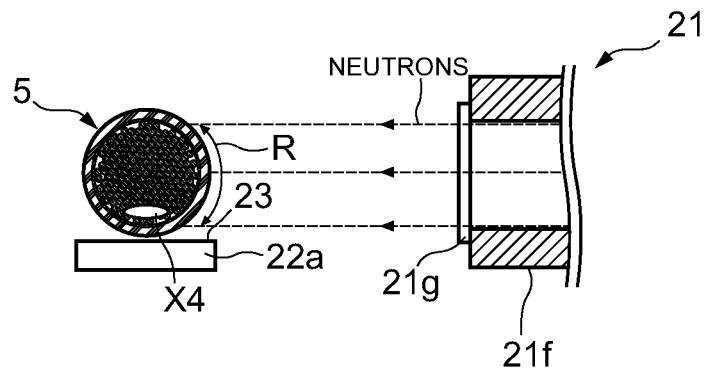

As in FIG. 6B and FIG. 6D, the two intermediate positions are on mutually opposite sides with respect to the cable 5.

In the case where the water region X1 of FIG. 6A exists, when the neutron detector 22a is arranged at the front position near the water region X1 as illustrated in this drawing, the neutron detector 22a can detect the target neutrons that are derived from the water region X1 and of which number is significantly larger than that in the case where the neutron detector 22a is arranged at either of the opposite position and the intermediate position. Also in each case of the water regions X2 to X4 in FIG. 6B to FIG. 6D, when the neutron detector 22a is arranged at the opposite position or the intermediate position near this water region, the neutron detector 22a can detect the target neutrons that are derived from this water region and of which number is significantly larger than that in each of the other arrangements. In actual inspection, an inside of the cable 5 cannot be seen from outside the cable 5, and for this reason, an arrangement of the neutron detectors 22a may be changed to arrangements such as the respective arrangements in FIG. 6A to FIG. 6D in the peripheral direction, and the inspection may be performed for each of the arrangements.

Figure 7:
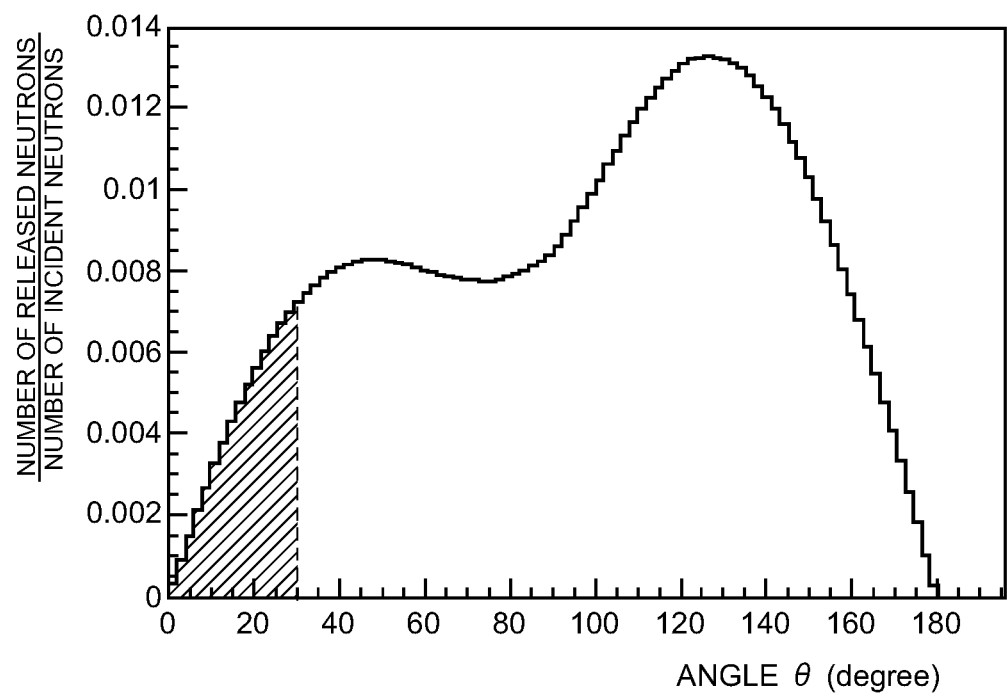
FIG. 7 illustrates a result of simulation concerning the case where a neutron beam is emitted to a solid cylindrical iron block, and illustrates the number of the neutrons scattered inside the iron block and released to an outside of the iron block.

FIG. 7 illustrates a result of simulation concerning the case where a neutron beam is emitted to a solid cylindrical iron block from a side surface of the iron block, and illustrates the number of the neutrons scattered inside the iron block and released to an outside of the iron block. In FIG. 7, the horizontal axis indicates an angle θ of viewing from a center point in the iron block. This center point is a center point of a part where an extension of the incident neutron beam intersects with an axis of the above-mentioned solid cylinder block. The angle θ is the angle made between the incident direction of the neutron beam to the iron block and a direction of the viewing. In FIG. 7, the vertical axis indicates, as a ratio to the number of the incident neutrons, the number of the neutrons scattered inside the iron block so as to be released to an outside of the iron block. More specifically, the vertical axis in FIG. 7 indicates, for the corresponding angle θ, the ratio of the number of the neutrons passing through a minute region existing in the direction of this angle θ when viewed from the center point. This minute region is a part of a surface of a sphere whose center is the center point and whose radius r is the same as a radius of the above-mentioned solid cylinder block. The minute region has an area of $2\pi r^2 \sin\theta d\theta$. Concerning FIG. 7, the number of the released neutrons is normalized by the number of the incident neutrons, and numerical values indicated by the vertical axis are values as an example.

As indicated by the hatched area in FIG. 7, a significant number of neutrons are scattered inside the iron block so as to be released to a side opposite to an irradiation region of the neutron beam. Specifically, the number of the neutrons released at an angle within 30 degrees from the incident direction is 7.6% of the total number of the scattered and released neutrons. Thus, even when the metal wire 11 of the cable 5 is a steel wire whose main component is iron, neutrons can be detected even at the above-described opposite position that is on a side opposite to the irradiation region. Accordingly, it can be said that a large number of target neutrons moderated by water inside the cable 5 can be detected even at the opposite position.

(Cable Inspection Method)

Figure 8:
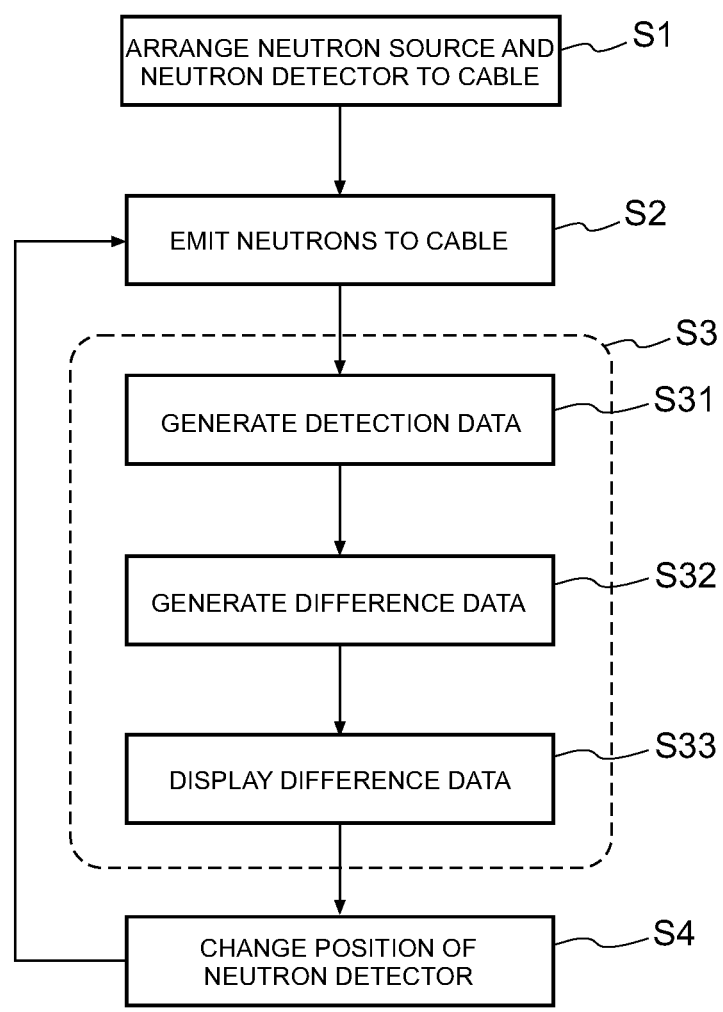
FIG. 8 is a flowchart illustrating a cable inspection method according to the first embodiment of the present invention.

FIG. 8 is a flowchart illustrating a cable inspection method according to the first embodiment of the present invention. This cable inspection method is a method for inspecting the cable 5 for supporting a bridge, and is performed using the above-described cable inspection device 10. The cable inspection method includes steps S1 to S4.

At the step S1, the neutron source 21 and the neutron detector 22a are arranged in relation to the cable 5 (that is in a state of supporting the bridge). The neutron source 21 is arranged at a position for emitting neutrons to a desired region (irradiation region) on an outer peripheral surface of the cable 5. In the present embodiment, the neutron detector 22a is arranged, for example, at the above-described front position, the above-described opposite position, or the above-described intermediate position. At this time, the neutron source 21 and the neutron detector 22a may be supported by an unillustrated appropriate support structure or support device.

At the step S2, the neutron source 21 emits neutrons (e.g., a pulsed neutron beam) to the irradiation region on the outer peripheral surface of the cable 5.

At the step S3, the neutron detection device 22 detects target neutrons released from the cable 5 to an outside of the cable 5 as a result of the step S2, and measures the number of the detected target neutrons. In the present embodiment, the neutron detection device 22 detects the target neutrons released from the cable 5 and incident on the detection surface 23 as a result of the step S2, and measures the number of the detected target neutrons. The step S3 may include steps S31 to S33.

At the step S31, the neutron detector 22a outputs the above-described detection signals for each position on the detection surface 23, and the data generation device 22b generates and outputs detection data that represent, for each position on the detection surface 23, the number of the target neutrons incident on this position.

At the step S32, the data processing unit 22d generates and outputs difference data that represent, for each position on the detection surface 23, a difference between the number of the incident neutrons in the reference data and the number of the incident neutrons in the detection data output at the step S31.

At the step S33, the display unit 22e displays, on its screen, the difference data output at the step S32. For example, the display unit 22e displays, as the difference data, data such as those illustrated in FIG. 16 described below.

At the step S4, a position of the neutron detector 22a is changed in the peripheral direction while the position of the neutron source 21 in relation to the cable 5 is kept constant (i.e., the irradiation region is kept constant). Then, the steps S2 and S3 are performed again. The steps S2 to S4 are repeated in this manner so that the steps S2 and S3 are performed for each peripheral-direction position of the neutron detector 22a. These peripheral-direction positions may be, for example, the above-described front position, the above-described opposite position, and the above-described two intermediate positions opposite each other with respect to the cable 5.

Such repeating of the steps S2 to S4 can implement the inspection in which a position of the neutron detector 22a is changed. Thereby, it can be found that water exists near the position of the neutron detector 22a corresponding to the difference data that most strongly indicate existence of water.

Although the above description is made on the case where a position of the neutron source 21 in relation to the cable 5 is constant, a position of the neutron source 21 (irradiation region) may be changed in the cable longitudinal direction, and the steps S2 to S4 may be repeated for each of the irradiation regions as described above. In this case, inspection is preferably performed with a longitudinal end portion of the cable 5 being preferentially set as an irradiation region. This is because a possibility of water existence tends to be higher in the longitudinal end portion of the cable 5 than that in the remaining portions of the cable 5.

Experiment Example 1

Figure 9A:
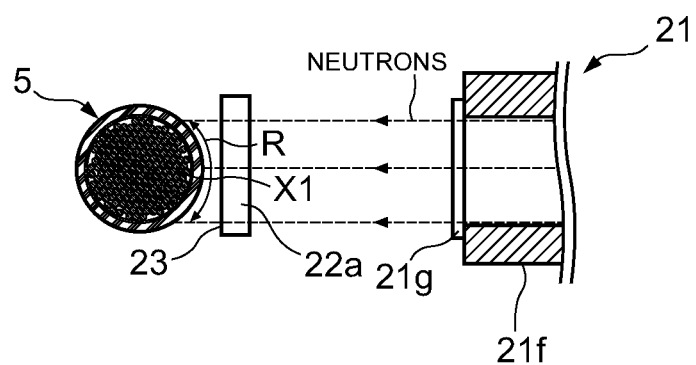
FIG. 9A and FIG. 9B each illustrate an arrangement of the neutron source, the neutron detector, and the cable in an experiment example 1.
Figure 9B:
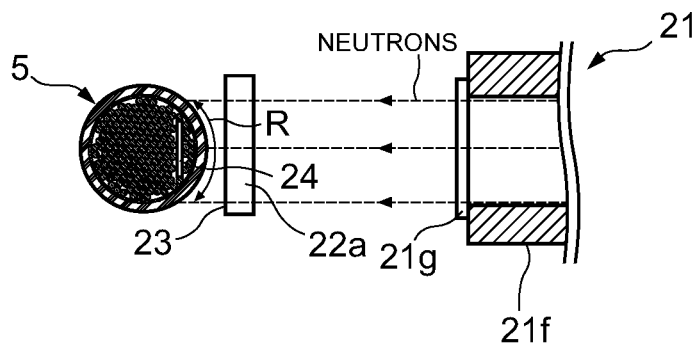

FIG. 9A and FIG. 9B each illustrate an arrangement of the neutron source 21, the neutron detector 22a, and the cable 5 in inspection of the cable 5 by the cable inspection device 10. A position of the neutron detector 22a in each of FIG. 9A and FIG. 9B corresponds to the above-described front position. In the case of FIG. 9A, the sound cable 5 containing no water inside is arranged. In the case of FIG. 9B, an acrylic plate is arranged inside the cable 5. A hydrogen density in acryl is almost the same as that in water, and neutrons easily react with hydrogen. Accordingly, the acrylic plate 24 can be regarded as water.

Each of the metal wires 11 of the cable 5 used in the experiment example 1 is a steel wire, an outer diameter of a bundle of the steel wires 11 is 100 mm, and this bundle is arranged inside a protective tube 12 made of polyethylene. The acrylic plate 24 used in the experiment example 1 has a rectangular parallelepiped shape, a thickness of 5 mm, a dimension (a dimension in a direction perpendicular to the paper surface of the drawing) of 300 mm in the cable longitudinal direction, and a dimension of 50 mm in its width direction.

For each of FIG. 9A and FIG. 9B, the inspection was performed using the cable inspection device 10. In other words, a neutron beam was emitted to the cable 5 by the neutron source 21, and target neutrons from the cable 5 were detected by the neutron detector 22a. The neutron beam was emitted to the cable 5 such that when viewed in an emission direction of the neutron beam to the cable 5, the irradiation region was included in an existence range of the acrylic plate 24 in the longitudinal direction of the cable 5. The inspection for each of FIG. 9A and FIG. 9B was performed under the same conditions, except that the acrylic plate 24 was arranged inside the cable 5 in FIG. 9B instead of some of the metal wires 11.

Figure 10A:
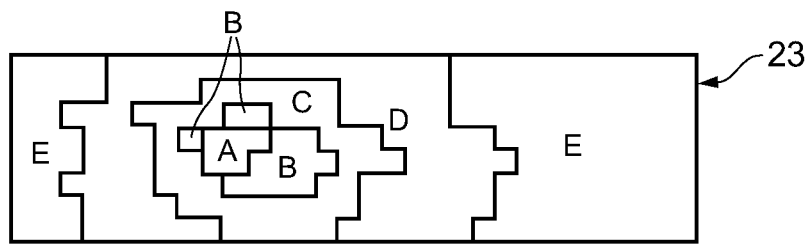
FIG. 10A and FIG. 10B each illustrate a result of inspection in the experiment example 1, and each express the number of neutrons incident on a unit area in a detection surface.
Figure 10B:
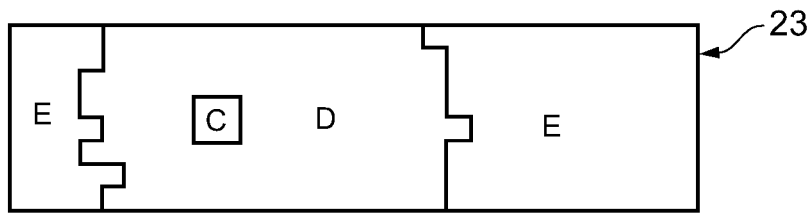

FIG. 10A and FIG. 10B illustrate results of the inspection for the cases of FIG. 9B and FIG. 9A, respectively. In each of FIG. 10A and FIG. 10B, the large rectangle represents the two-dimensional detection surface 23 when viewed in the left-right direction in FIG. 9A or 9B. The detection surface 23 is a part of the actual detection surface 23 in the longitudinal direction, and a longitudinal-direction range of this part is the same as that of the acrylic plate 24. The data in FIG. 10A and FIG. 10B represent the number of the target neutrons incident on the detection surface 23 over a measurement period of 10 minutes, and the measurement start time point is the time when the pulsed neutron beam was emitted to the cable 5.

In FIGS. 10A and 10B, the regions A to E on the detection surface 23 are regions that differ from each other in the number of the incident target neutrons per unit area. The region A is a region where the number of the incident target neutrons per unit area is approximately equal to or larger than 2500 and smaller than 3000. The region B is a region where the number of the incident target neutrons per unit area is approximately equal to or larger than 2000 and smaller than 2500. The region C is a region where the number of the incident target neutrons per unit area is approximately equal to or larger than 1500 and smaller than 2000. The region D is a region where the number of the incident target neutrons per unit area is approximately equal to or larger than 1000 and smaller than 1500. The region E is a region where the number of the incident target neutrons per unit area is approximately smaller than 1000.

In the case of FIG. 10A where the acrylic plate 24 (water) exists inside the cable 5, the number of the detected incident target neutrons is substantially larger than that in the case of FIG. 10B where the cable 5 is sound. Accordingly, based on the number of detected incident target neutrons, it can be detected whether water exists inside the cable 5.

Experiment Example 2

FIG. 11A to FIG. 11D each illustrate an arrangement of the neutron source 21, the neutron detector 22a, and the cable 5 in inspection of the cable 5 by the cable inspection device 10. A position of the neutron detector 22a in each of FIG. 11A to FIG. 11D corresponds to the above-described front position. In each of FIG. 11A to FIG. 11D, four acrylic plates 24 are stacked inside the cable 5. The position of the four acrylic plates 24 differ among FIG. 11A to FIG. 11D, but positions of the neutron source 21 and the neutron detector 22a are the same for FIG. 11A to FIG. 11D.

A structure (materials, dimensions, and the like) of the cable 5 used in the experiment example 2 is the same as that of the cable 5 used in the experiment example 1. A structure (dimensions, a shape, and the like) of each acrylic plate 24 used in the experiment example 2 is the same as that of the acrylic plate 24 used in the experiment example 1.

For each of FIG. 11A to FIG. 11D, the inspection was performed using the cable inspection device 10. In other words, a neutron beam was emitted to the cable 5 by the neutron source 21, and target neutrons from the cable 5 were detected by the neutron detector 22a. The neutron beam was emitted to the cable 5 such that when viewed in an emission direction of the neutron beam to the cable 5, an irradiation region was included in an existence range of the acrylic plates 24 in the cable longitudinal direction. The inspection for each of FIG. 11A to FIG. 11D was performed under the same conditions, except that a position of the four acrylic plates 24 differs among FIG. 11A to FIG. 11D.

FIG. 12A to FIG. 12D illustrate results of the inspection for the cases of FIG. 11A to FIG. 11D, respectively. In each of FIG. 12A to FIG. 12D, the large rectangle represents the two-dimensional detection surface 23 when viewed in the left-right direction in FIG. 11A to FIG. 11D. The detection surface 23 is a part of the actual detection surface 23 in the longitudinal direction, and a longitudinal-direction range of this part is the same as that of the acrylic plates 24. The data in FIG. 12A to FIG. 12D represent the number of the target neutrons incident on the detection surface 23 over a measurement period of 10 minutes, and the measurement start time point is the time when the pulsed neutron beam was emitted to the cable 5.

FIG. 12A to FIG. 12D each illustrate a ratio of the number of the incident target neutrons per unit area at each position on the detection surface 23, to a reference value at this position. Here, the reference value is the number of the incident target neutrons when the four acrylic plates 24 are not arranged inside the cable 5. Specifically, the reference value is the number of the incident target neutrons at each position on the detection surface 23 in FIG. 9A described above.

Figure 12A:
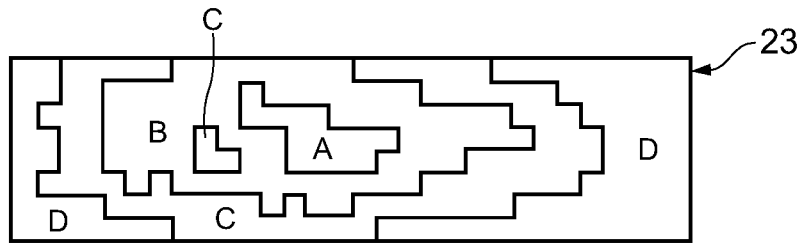
FIG. 12A to FIG. 12D each illustrate a result of inspection in the experiment example 2, and each express the number of neutrons incident on a unit area in the detection surface.

In FIG. 12A, the region A is a region where the ratio is approximately equal to or larger than 7 and smaller than 8, the region B is a region where the ratio is approximately equal to or larger than 6 and smaller than 7, the region C is a region where the ratio is approximately equal to or larger than 4 and smaller than 6, and the region D is a region where the ratio is approximately equal to or larger than 2 and smaller than 4.

Figure 12B:
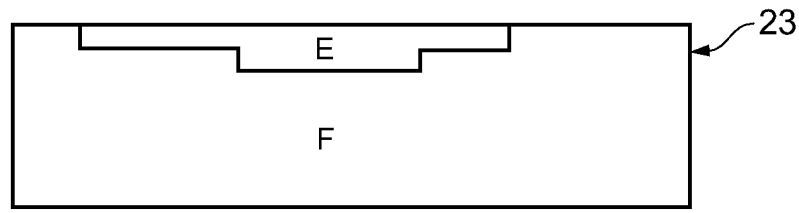
Figure 12C:
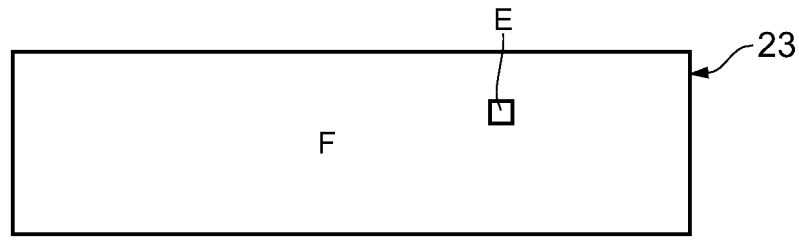

In FIGS. 12B and 12C, the region E is a region where the ratio is approximately equal to or larger than 2 and smaller than 3, and the region F is a region where the ratio is approximately smaller than 2.

Figure 12D:
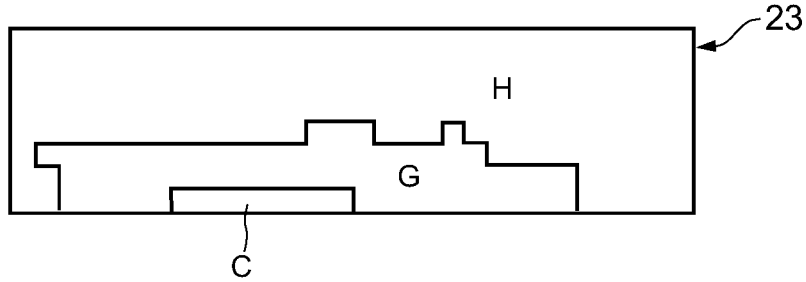

In FIG. 12D, the region C is a region where the ratio is approximately equal to or larger than 4 and smaller than 6, the region G is a region where the ratio is approximately equal to or larger than 3 and smaller than 4, and the region H is a region where the ratio is approximately smaller than 3.

Figure 11A:
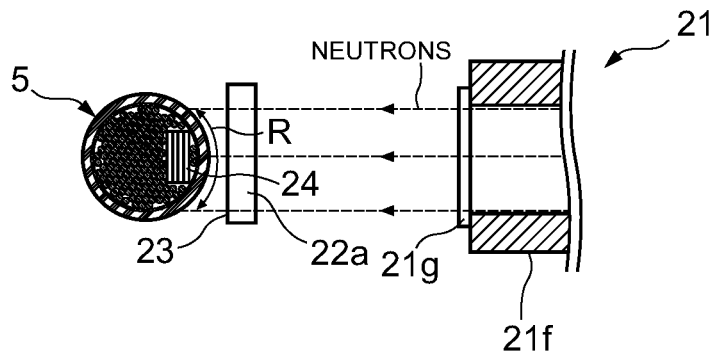
FIG. 11A to FIG. 11D each illustrate an arrangement of the neutron source, the neutron detector, and the cable in an experiment example 2.
Figure 11B:
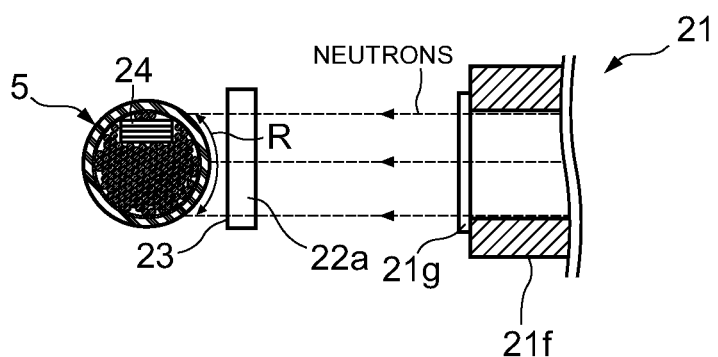
Figure 11C:
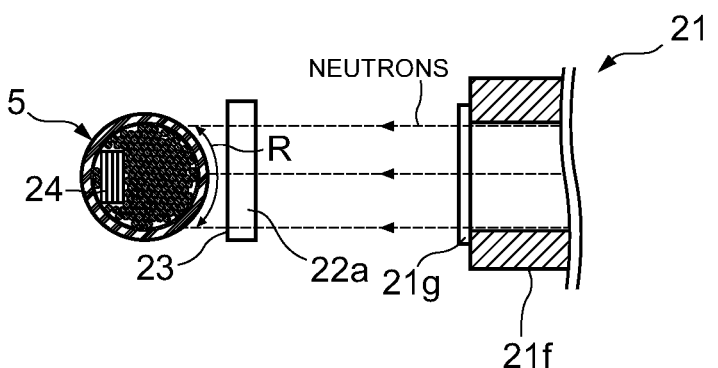
Figure 11D:
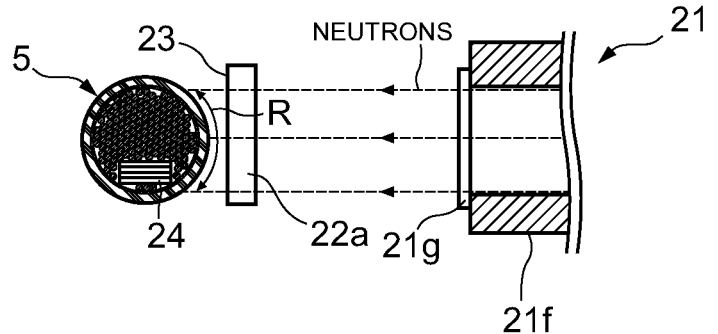

As illustrated in FIG. 11A and FIG. 12A, when the neutron detector 22a is arranged at a position close to the acrylic plates 24 (water) inside the cable 5 and facing the acrylic plates 24, a region where the ratio is equal to or larger than 7 appears on the detection surface 23, and the number of the target neutrons incident on the detection surface 23 is significantly larger than that in the other arrangements (FIG. 11B to FIG. 11D) of the neutron detector 22a.

Experiment Example 3

FIG. 13A to FIG. 13D each illustrate an arrangement of the neutron source 21, the neutron detector 22a, and the cable 5 in inspection of the cable 5 by the cable inspection device 10. A position of the neutron detector 22a in each of FIG. 13A to FIG. 13D corresponds to the above-described opposite position. In each of FIG. 13A to FIG. 13D, one acrylic plate 24 is arranged inside the cable 5. A position of the acrylic plate 24 differs among FIG. 13A to FIG. 13D, but positions of the neutron source 21 and the neutron detector 22a are the same for FIG. 13A to FIG. 13D.

A structure of the cable 5 used in the experiment example 3 is the same as that of the cable 5 used in the experiment example 1. A structure of each acrylic plate 24 used in the experiment example 3 is the same as that of the acrylic plate 24 used in the experiment example 1.

For each of FIG. 13A to FIG. 13D, the inspection was performed using the cable inspection device 10. In other words, a neutron beam was emitted to the cable 5 by the neutron source 21, and target neutrons from the cable 5 were detected by the neutron detector 22a. The neutron beam was emitted to the cable 5 such that when viewed in an emission direction of the neutron beam to the cable 5, an irradiation region was included in an existence range of the acrylic plate 24 in the cable longitudinal direction. The inspection for FIG. 13A to FIG. 13D was performed under the same conditions, except that a position of the acrylic plate 24 differs among FIG. 13A to FIG. 13D.

FIG. 14A to FIG. 14D illustrate results of the inspection for the cases of FIG. 13A to FIG. 13D, respectively. In each of FIG. 14A to FIG. 14D, the large rectangle represents the two-dimensional detection surface 23 when viewed in the left-right direction in FIG. 13A to FIG. 13D. The detection surface 23 is a part of the actual detection surface 23 in the longitudinal direction, and a longitudinal-direction range of this part is the same as that of the acrylic plate 24. The data in FIG. 14A to FIG. 14D represent the number of the target neutrons incident on the detection surface 23 over a measurement period of 10 minutes, and the measurement start time point is the time when the pulsed neutron beam was emitted to the cable 5.

FIG. 14A to FIG. 14D each illustrate a ratio of the number of the incident target neutrons per unit area at each position on the detection surface 23, to a reference value at this position. Here, the reference value is the number of target neutrons incident at each position on the detection surface 23 when a plurality of the steel wires 11 are arranged instead of the acrylic plate 24 in FIG. 13A.

In FIG. 14A to FIG. 14D, the region A is a region where the ratio is approximately equal to or larger than 1.6 and smaller than 2.0, the region B is a region where the ratio is approximately equal to or larger than 1.4 and smaller than 1.6, the region C is a region where the ratio is approximately equal to or larger than 1.0 and smaller than 1.4, the region D is a region where the ratio is approximately equal to or larger than 1.2 and smaller than 1.4, the region E is a region where the ratio is approximately equal to or larger than 1.0 and smaller than 1.2, the region F is a region where the ratio is approximately equal to or larger than 1.2 and smaller than 1.3, the region G is a region where the ratio is approximately equal to or larger than 1.1 and smaller than 1.2, and the region H is a region where the ratio is approximately equal to or larger than 1.0 and smaller than 1.1.

Figure 13A:
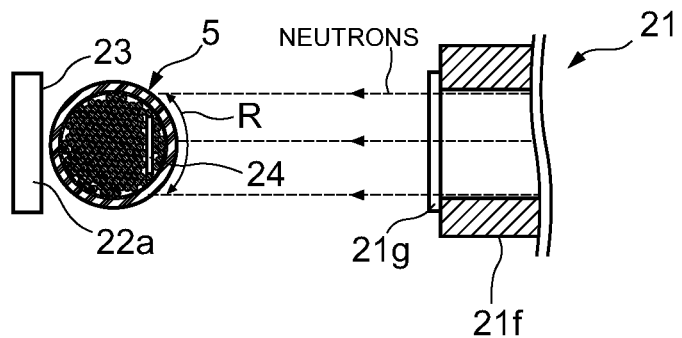
FIG. 13A to FIG. 13D each illustrate an arrangement of the neutron source, the neutron detector, and the cable in an experiment example 3.
Figure 13B:
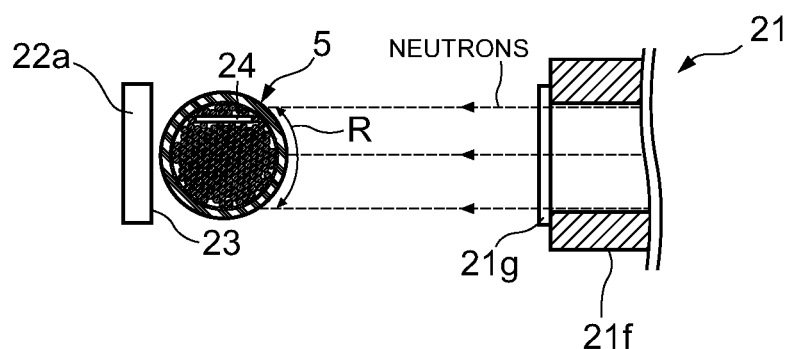
Figure 13C:
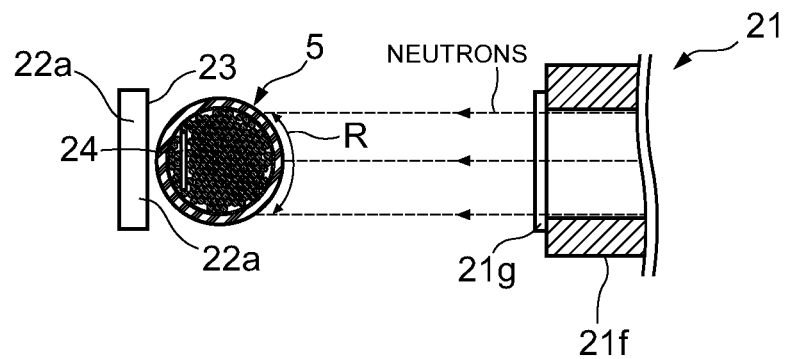
Figure 13D:
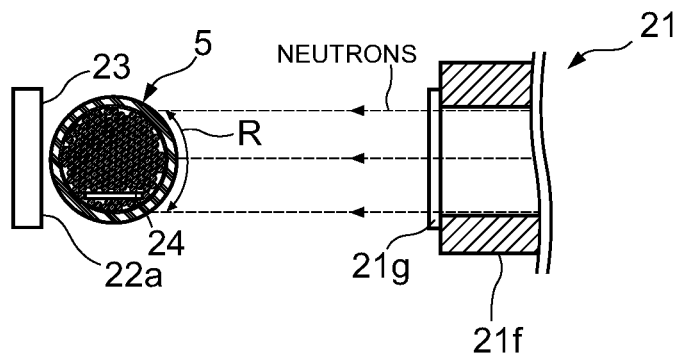
Figure 14A:
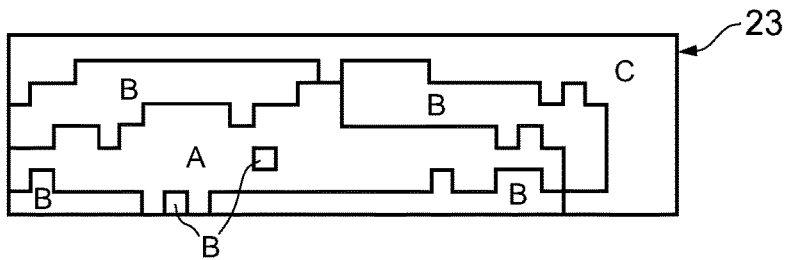
FIG. 14A to FIG. 14D each illustrate a result of inspection in the experiment example 3, and each express the number of neutrons incident on a unit area in the detection surface.
Figure 14B:
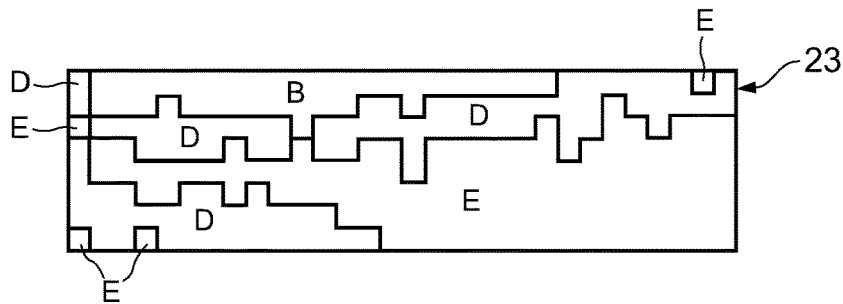
Figure 14C:
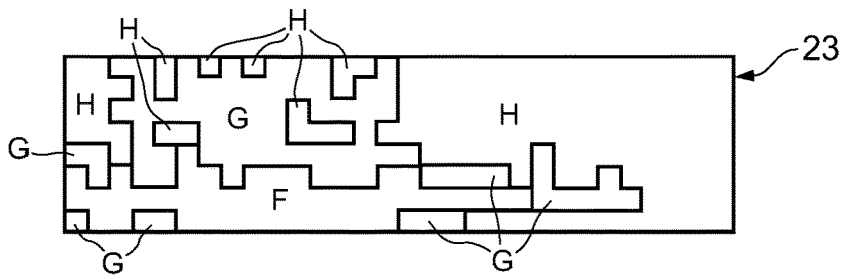
Figure 14D:
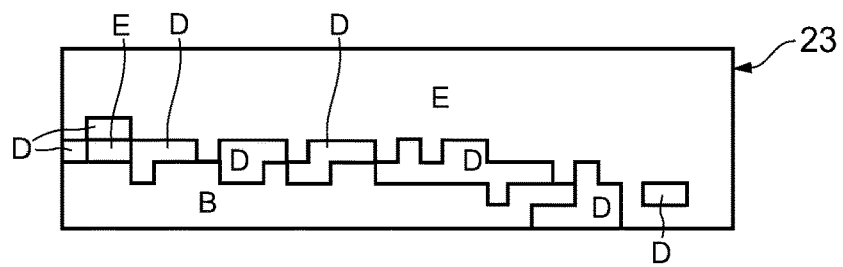

As illustrated in FIG. 13A to FIG. 13D and FIG. 14A to FIG. 14D, it can be understood that even when the neutron detector 22a is arranged at the opposite position, the number of the incident target neutrons is significantly larger than that when the acrylic plate 24 is not provided. Thus, even when the neutron detector 22a is arranged at the opposite position, it can be inspected whether water exists inside the cable 5. It can be understood that even when the acrylic plate 24 exists on an opposite side of the irradiation region as illustrated in FIG. 13C, the acrylic plate 24 (water) can be detected by the neutron detector 22a arranged near the acrylic plate 24 in FIG. 13C.

Experiment Example 4

Figure 15:
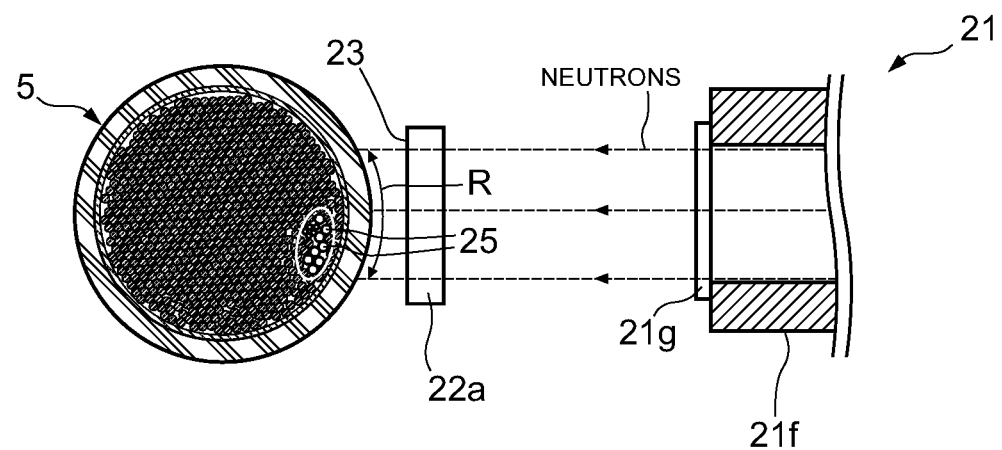
FIG. 15 illustrates an arrangement of the neutron source, the neutron detector, and the cable in an experiment example 4.

FIG. 15 illustrates an arrangement of the neutron source 21, the neutron detector 22a, and the cable 5 in the inspection of the cable 5 by the cable inspection device 10. A position of the neutron detector 22a in FIG. 15 corresponds to the above-described front position.

Each of the metal wires 11 of the cable 5 used in the experiment example 4 is a steel wire, an outer diameter of a bundle of the steel wires 11 is 185 mm, and this bundle is arranged inside the protective tube 12 made of polyethylene. In the experiment example 4, eight acrylic rods 25 having a diameter of 6 mm and five acrylic rods 25 having a diameter of 1 mm were arranged inside the cable 5 in a region enclosed by the white ellipse as illustrated in FIG. 15. These acrylic rods 25 each have a length of 500 mm, and are arranged at the same longitudinal-direction position inside the cable 5.

For FIG. 15, the inspection was performed using the cable inspection device 10. In other words, a neutron beam was emitted to the cable 5 by the neutron source 21, and target neutrons from the cable 5 were detected by the neutron detector 22a. The neutron beam was emitted to the cable 5 such that when viewed in an emission direction of the neutron beam to the cable 5, an irradiation region was included in an existence range of the acrylic rods 25 in the cable longitudinal direction.

Figure 16:
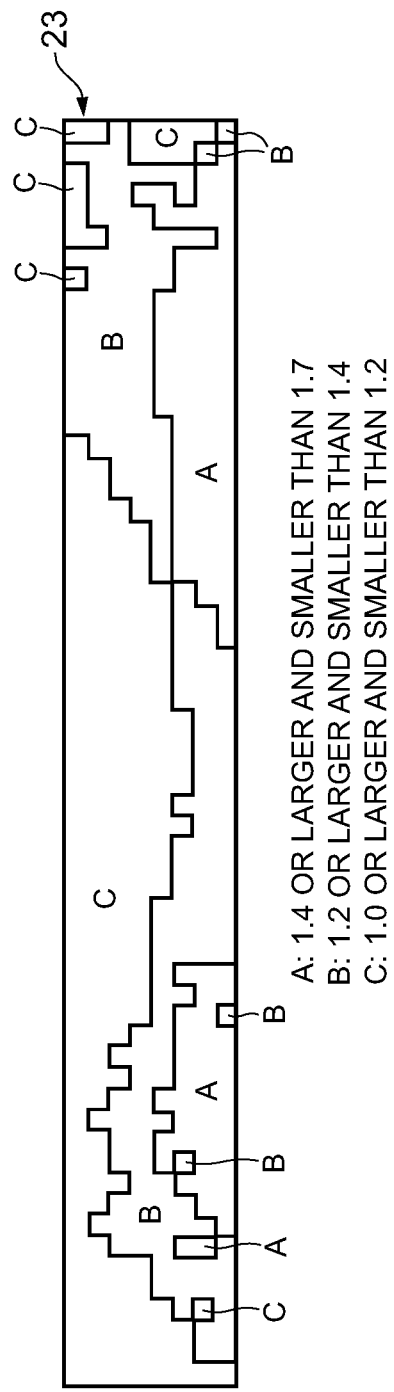
FIG. 16 illustrates a result of inspection in the experiment example 4, and expresses difference data of the number of neutrons incident on a unit area in the detection surface.

FIG. 16 illustrate a result of the inspection for FIG. 15. In FIG. 16, the large rectangle represents the two-dimensional detection surface 23 when viewed in the left-right direction in FIG. 15. The detection surface 23 is a part of the actual detection surface 23 in the longitudinal direction, and a longitudinal-direction range of this part is the same as that of the acrylic rods 25. The data in FIG. 16 represent the number of thermal neutrons incident on the detection surface 23 over a measurement period of 10 minutes, and the measurement start time point is the time when the pulsed neutron beam was emitted to the cable 5.

FIG. 16 represents difference data. In other words, FIG. 16 illustrates a difference between the number of the incident thermal neutrons per unit area at each position on the detection surface 23 and a reference value at this position. Here, the reference value is the number of incident thermal neutrons per unit area at each position on the detection surface 23 when no acrylic rods 25 are arranged inside the cable 5. Specifically, the reference value is the number of the incident thermal neutrons when a region of the acrylic rods 25 are filled with a plurality of steel rods in FIG. 15. Concerning the other matters, inspection in the case of determining the reference values was performed under the same conditions as those in the inspection for FIG. 15.

In FIG. 16, the difference at each position is expressed as a ratio to the minimum value of the difference. In other words, in FIG. 16, the region A is a region where the ratio is approximately equal to or larger than 1.4 and smaller than 1.7, the region B is a region where the ratio is approximately equal to or larger than 1.2 and smaller than 1.4, and the region C is a region where the ratio is approximately equal to or larger than 1.0 and smaller than 1.2.

In the case of existence of a region where the value (the ratio of the difference to its minimum value in this example) is substantially increased from zero (or one) as in the difference data in FIG. 16, it can be determined that water exists inside the cable 5. Thus, by seeing the difference data, it can be immediately recognized whether the value is substantially increased from zero (or one). It can be estimated that water exists at a position corresponding to a region where the value in the difference data is the highest.

Advantageous Effects of First Embodiment

According to the first embodiment described above, in the case where water exists inside the cable 5, when neutrons are emitted to the cable 5, the neutrons react with the water, and thus, reduce their own energies. For this reason, based on the number of the detected target neutrons corresponding to the neutrons having the reduced energies, it can be determined whether water exists inside the cable 5.

The neutron source 21 emits, to the cable 5, the neutrons including neutrons each of which has the resonance scattering energy. Thereby, a probability that the neutrons are scattered within the cable 5 becomes higher. Accordingly, a distance by which the neutrons travel inside the cable 5 becomes longer. As a result, the neutrons after being scattered are released from the outer peripheral surface of the cable 5 over a wide range in the peripheral direction and the longitudinal direction of the cable 5. Thus, over a range wider than the irradiation range, it can be inspected whether water exists inside the cable 5.

For example, a dimension of the detection surface 23 in the cable longitudinal direction may be larger than a dimension of the irradiation area in the cable longitudinal direction. In this case, when the number of the target neutrons incident on an area included in the detection surface 23 and shifted in the longitudinal direction from the irradiation region on the cable 5 is larger than a predetermined threshold value, it can be determined that water exists at a position inside the cable 5 and near this area (e.g., facing this area).

Second Embodiment

The following describes a second embodiment of the present invention, but the matters that are not described below may be the same as those in the case of the first embodiment.

(Configuration of Cable Inspection Device)

Figure 17:
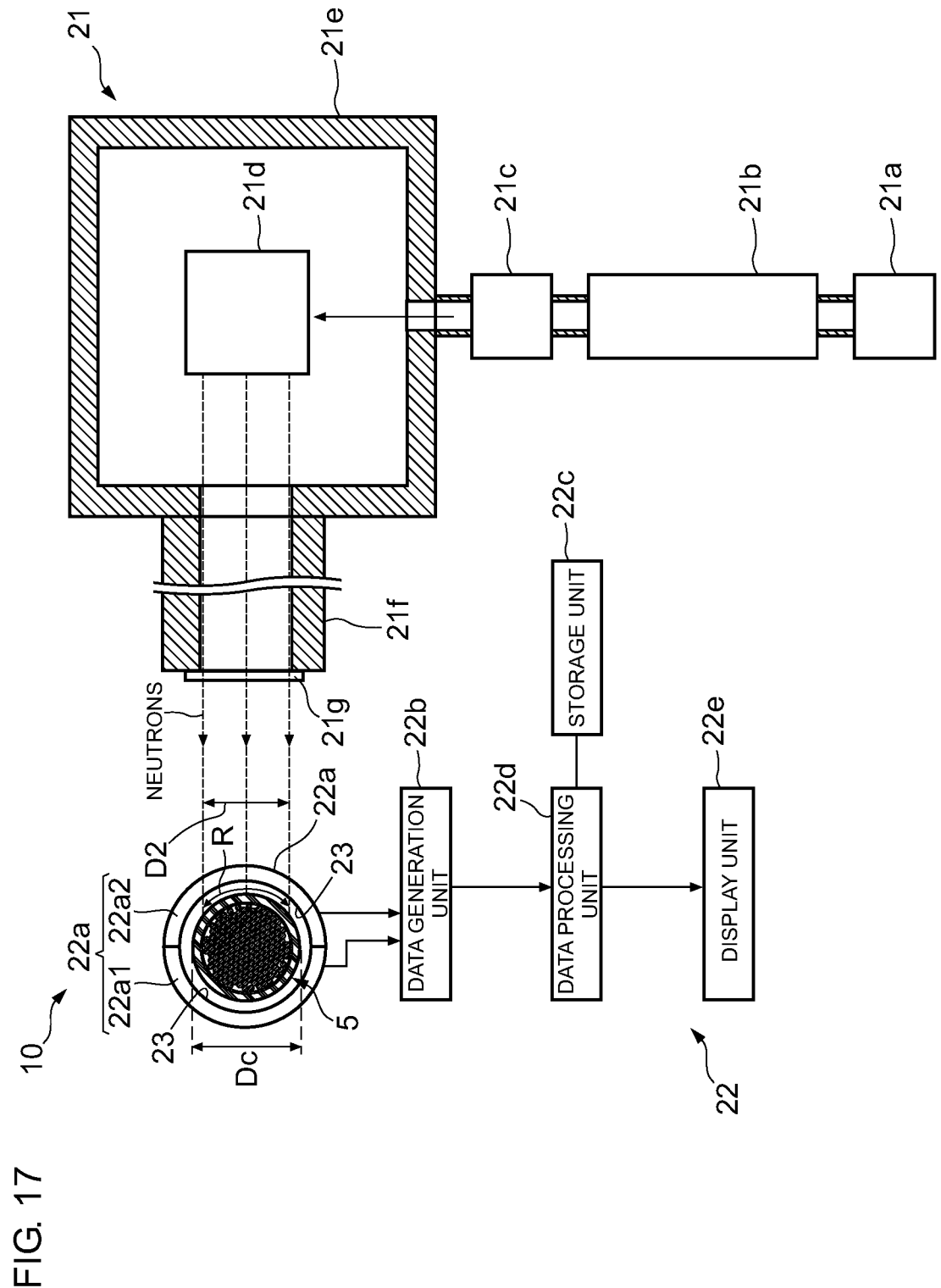
FIG. 17 illustrates a configuration example of a cable inspection device according to a second embodiment of the present invention.

FIG. 17 illustrates a configuration example of the cable inspection device 10 according to the second embodiment of the present invention. In the second embodiment, the detection surface 23 of the neutron detector 22a is formed so as to surround an inner space in a peripheral direction of the inner space in which the cable 5 can be arranged. In other words, the detection surface 23 surrounds the cable 5 in the peripheral direction of the cable 5, in a state where the neutron detector 22a is arranged such that the cable 5 is positioned in the inner space as in FIG. 17.

Such a neutron detector 22a (detection surface 23) may extend so as to make one complete circle in the peripheral direction of the inner space. In this case, the neutron detector 22a including the detection surface 23 may include a plurality of division portions (two division portions 22a1 and 22a2 in the example of FIG. 17) that are divided in the peripheral direction of the inner space. With this configuration, a plurality of the division portions can be arranged so as to surround the cable 5 in the peripheral direction. In this state, a plurality of the division portions may be joined to each other by appropriate coupling means. The appropriate coupling means may be, for example, a rope or tape wound on an entire outer periphery of the neutron detector 22 in the peripheral direction, or bolts coupling, to each other, flange portions provided on outer peripheral surfaces of the respective division portions, but are not limited to these. In a state of FIG. 17, each of the division portions 22a1 and 22a2 may be supported by an unillustrated support structure or support device.

Similarly to the first embodiment, based on respective detection signals output from the neutron detector 22a, the data generation unit 22b generates detection data that represent, for each position on the detection surface 23 (particularly for each position in the peripheral direction of the cable 5), the number of neutrons incident on this position. The data generation unit 22b outputs the generated detection data.

(Cable Inspection Method)

The cable inspection method according to the second embodiment of the present invention is performed using the cable inspection device 10 according to the second embodiment, and differs in the below-described matters from the cable inspection method of the first embodiment.

At the step S1, the neutron source 21 and the neutron detector 22a are arranged in relation to the cable 5. At this time, the neutron detector 22a is arranged so as to surround the cable 5 as described above with reference to FIG. 17.

The step S2 is the same as that in the case of the first embodiment.

At the step S31, the neutron detector 22a outputs the above-described detection signals for each position on the detection surface 23, and the data generation unit 22b outputs the detection data that represent, for each position on the detection surface 23, the number of the target neutrons incident on this position.

At the step S32, the data processing unit 22d generates and outputs the difference data that represent, for each position on the detection surface 23, a difference between the number of the incident target neutrons in the reference data and the number of the incident target neutrons in the detection data output at the step S31. The step S33 is the same as that in the case of the first embodiment.

Differently from the first embodiment, the step S4 is omitted, and the steps S2 to S4 are not repeated.

Advantageous Effects of Second Embodiment

According to the second embodiment described above, the neutron detector 22a can be arranged so as to surround the cable 4. Thus, differently from the first embodiment, it becomes unnecessary to change a position of the neutron detector 22a in the peripheral direction at the step S4.

The present invention is not limited to the above-described embodiments, and can be variously modified within the scope of the technical idea of the present invention. For example, the cable inspection device 10 and the cable inspection method do not need to include all of a plurality of the above-described matters, and may include only a part of a plurality of the above-described matters. The cable inspection device 10 and the cable inspection method do not need to achieve all of the above-described advantageous effects, and may achieve only a part of the above-described advantageous effects.

According to the present invention, for the first embodiment or the second embodiment described above, any one of the following modified examples 1 to 3 may be adopted, or two or all of the modified examples 1 to 3 may be adopted in any combination. In this case, the matters that are not described below may be the same as those in the first embodiment or the second embodiment described above.

Modified Example 1

The data processing unit 22d generates and outputs ratio data (processed data) that represent, for each position on the detection surface 23, a ratio between the number of the incident target neutrons in the reference data and the number of the incident target neutrons in the detection data (e.g., a ratio of the number of the incident target neutrons in the detection data to the number of the incident target neutrons in the reference data).

Modified Example 2

The data generation unit 22b may generate and output detection data that represent the total number of the target neutrons incident on the entire detection surface 23. In this case, the reference data may be data concerning the sound cable and representing the total number of the target neutrons incident on the entire detection surface 23, and the data processing unit 22d may generate and output processed data that represent a difference or ratio between the total number in the reference data and the total number in the detection data.

Modified Example 3

The neutron source 21 includes the ion source 21a, the acceleration device 21b, the target 21d, and the like in the above description, but does not need to include these constituents. In other words, the neutron source that emits neutrons to the cable 5 may be a radioisotope (RI) neutron source. This RI neutron source may be $^{252}$Cf, for example, but is not limited to this.

REFERENCE SIGNS LIST

1 Cable-stayed bridge
2 Pier
3 Tower
4 Bridge girder
5 Cable
10 Cable inspection device
11 Metal wire (steel wire)
12 Cover layer (protective tube)
13 Restriction portion
21 Neutron source
21a Ion source
21b Acceleration device
21c Beam adjuster
21d Target
21e Container
21f Tubular shielding member
21g Thermal neutron shielding member
22 Neutron detection device
22a Neutron detector
22a1, 22a2 Division portion
22b Data generation unit
22c Storage unit
22d Data processing unit
22e Display unit
23 Detection surface
24 Acrylic plate
25 Acrylic rod

The invention claimed is:

1. A cable inspection device for non-destructively inspecting a cable, the cable being configured so as to include a plurality of metal wires, the cable inspection device comprising:
a neutron source that emits neutrons to an irradiation region on an outer peripheral surface of the cable; and
a neutron detection device that includes a detection surface arranged outside the cable and that detects target neutrons when the neutron source emits neutrons to the cable, wherein the target neutrons are among the neutrons released from the cable and incident on the detection surface, and each have an energy equal to or lower than a predetermined value that is lower than an energy of a fast neutron,
wherein in a longitudinal direction of the cable, the detection surface includes a part positioned within the irradiation region and a part positioned outside the irradiation region, and
the neutron detection device further includes:
a data generation unit that generates detection data, the detection data representing, for each of multiple positions on the detection surface in the longitudinal direction, a number of the target neutrons incident on the position;
a storage unit that stores reference data corresponding to the detection data, the reference data representing, for each of the positions on the detection surface in the longitudinal direction, a number of the target neutrons incident on the position when the neutrons are emitted to a sound cable having a same structure as a structure of the inspected cable, where the number in the reference data varies depending on the position in the longitudinal direction; and
a data processing unit that generates processed data that represent, for each of the positions in the longitudinal direction, a difference or a ratio between the number in the reference data and the number in the detection data.

2. The cable inspection device according to claim 1, wherein each of the metal wires is a steel wire formed of steel.

3. The cable inspection device according to claim 1, wherein an energy of a neutron that is resonantly scattered due to the metal wire when the neutron is made incident on the metal wire is defined as a resonance scattering energy, and
the neutron source emits, to the cable, the neutrons including neutrons each having the resonance scattering energy.

4. The cable inspection device according to claim 1, the neutron detection device including:
a neutron detector that includes the detection surface, wherein each time the target neutron is incident on the detection surface, the neutron detector outputs a detection signal indicating the position that is included in the detection surface and on which the target neutron is incident; and
the data generation unit that generates, based on each of the detection signals, the detection data representing the number of the incident target neutrons for each of the positions on the detection surface, and outputs the detection data.

5. The cable inspection device according to claim 4, wherein the detection surface is formed so as to surround an inner space in a peripheral direction of the inner space in which the cable can be arranged.

6. A cable inspection method for non-destructively inspecting a cable, the method comprising:
(A) arranging a neutron source and a neutron detector in relation to the cable that is configured so as to include a plurality of metal wires;
(B) by the neutron source, emitting neutrons to an irradiation region on an outer peripheral surface of the cable; and
(C) detecting target neutrons, wherein the target neutrons are among the neutrons released from the cable as a result of the emitting and incident on a detection surface of the neutron detector, and each have an energy equal to or lower than a predetermined value that is lower than an energy of a fast neutron,
wherein in a longitudinal direction of the cable, the detection surface includes a part positioned within the irradiation region and a part positioned outside the irradiation region,
the method further comprises:
at (C), acquiring reference data, then generating detection data, the detection data representing, for each of multiple positions on the detection surface in the longitudinal direction, a number of the target neutrons incident on the position,
the reference data representing, for each of the positions on the detection surface in the longitudinal direction, a number of the target neutrons incident on the position when the neutrons are emitted to a sound cable having a same structure as a structure of the inspected cable, where the number in the reference data varies depending on the position in the longitudinal direction; and
at (C), generating processed data that represent, for each of the positions in the longitudinal direction, a difference or a ratio between the number in the reference data and the number in the detection data.

7. The cable inspection method according to claim 6, comprising, at (A), arranging the neutron detector such that the detection surface surrounds the cable in a peripheral direction of the cable.

8. The cable inspection method according to claim 6, comprising performing (B) and (C) in a state where the neutron detector is arranged by (A) at a front position, an opposite position, or an intermediate position,
the front position being a position facing the irradiation region,
the opposite position being a position facing an opposite region that is on the outer peripheral surface and is positioned on a side opposite to the irradiation region,
the intermediate position being a position facing an intermediate region that is on the outer peripheral surface and is positioned intermediately between the irradiation region and the opposite region in a peripheral direction of the cable.

9. A cable inspection method for non-destructively inspecting a cable, the method comprising:
(A) arranging a neutron source and a neutron detector in relation to the cable that is configured so as to include a plurality of metal wires;
(B) by the neutron source, emitting neutrons to an irradiation region on an outer peripheral surface of the cable; and
(C) detecting target neutrons and measuring the number of the detected target neutrons, wherein the target neutrons are among the neutrons released from the cable as a result of the emitting and incident on a detection surface of the neutron detector, and each have an energy equal to or lower than a predetermined value that is lower than an energy of a fast neutron,
wherein the method further comprises performing (B) and (C) in a state where the neutron detector is arranged by (A) at a front position, an opposite position, or an intermediate position,
the front position being a position facing the irradiation region,
the opposite position being a position facing an opposite region that is on the outer peripheral surface and is positioned on a side opposite to the irradiation region,
the intermediate position being a position facing an intermediate region that is on the outer peripheral surface and is positioned intermediately between the irradiation region and the opposite region in a peripheral direction of the cable,
wherein as the intermediate position, there are first and second intermediate positions opposite to each other with respect to the cable, and
the method further comprises repeating (A) to (C) so as to arranging, at (A) of each time, the neutron detector at one of the front position, the opposite position, the first intermediate position, and the second intermediate position, and performing (B) and (C) for each arrangement of the front position, the opposite position, the first intermediate position, and the second intermediate position.

10. The cable inspection method according to claim 9, wherein a dimension of the detection surface in a longitudinal direction of the cable is larger than a dimension of the irradiation region in the longitudinal direction.

11. The cable inspection method according to claim 6, wherein a dimension of the detection surface in a longitudinal direction of the cable is equal to or larger than two times an outer diameter of the cable.

* * * * *